United States Patent [19]
Caldwell

[11] Patent Number: 5,478,722
[45] Date of Patent: Dec. 26, 1995

[54] PRESERVED CELL PREPARATIONS FOR FLOW CYTOMETRY AND IMMUNOLOGY

[75] Inventor: Charles W. Caldwell, Columbia, Mo.

[73] Assignee: The Curators of the University of Missouri, Columbia, Mo.

[21] Appl. No.: 652,095

[22] Filed: Feb. 17, 1991

[51] Int. Cl.$^6$ .............................. C12N 9/50; A01N 1/02; C12Q 1/00; G01N 33/53

[52] U.S. Cl. .................. 435/1.1; 435/2; 435/7.1; 435/7.2; 435/7.21; 435/240.1; 435/219

[58] Field of Search ................... 435/7.4, 1, 2, 240.1, 435/240.2, 240.3, 219, 7.1, 7.2

[56] References Cited

U.S. PATENT DOCUMENTS

| | | | |
|---|---|---|---|
| 3,682,776 | 8/1972 | Grundmann et al. | 435/1 |
| 4,591,572 | 5/1986 | Mattes et al. | 436/538 |
| 4,857,451 | 8/1989 | Schwartz | 435/7 |

FOREIGN PATENT DOCUMENTS

| | | |
|---|---|---|
| 61-079163 | 9/1986 | Japan. |
| 01259261 | 4/1988 | Japan. |

OTHER PUBLICATIONS

D. Levitt & M. King, "Methanol Fixation . . ." *Journal of Immunological Methods* 96: 233–237 (1987).

R. W. Schroff et al, "Detection of Intra-Cytoplasmic Antigens . . ." *Journal of Immunological Methods* 70:167–177 (1984).

L. Harvath, "Quality control in clinical flow cytometry," *Pathology and Immunopathology Research* 7: 338–344 (1988).

P. K. Horan et al, "Standards and Controls in Flow Cytometry," chapter 21 (pp. 397–414) in Melamed et al, eds., *Flow Cytometry and Sorting*, 2nd edition, Wiley & Liss, New York (1990).

A. Feldman and R. W. Dapson, "The Chemistry of Fixation and Staining, Part I: Basic Concepts", *J. Histotechnology* 3(4): 132–135 (1980).

R. W. Dapson and A. Feldman, "The Chemistry of Fixation and Staining, Park II: A Unified Theory of Acid/Base Staining Reactions," *J. Histotechnology* 3(4): 138–142 (1980).

C. W. Caldwell et al, "Fluorescence Intensity as a Quality Control Parameter in Clinical Flow Cytometry," *Amer. J. Clinical Pathology* 88(4): 447–456 (1987).

Sales literature on Cyto-Trol™ lyophilized cells, distributed by Coulter Company.

Babcock, G. F., et al, "Use of Previously Fixed Lymphocytes for Immunophenotyping," Abstract #544B, *Cytometry, Suppl.* 5 (p. 102), 1991.

Lal, R. B., et al, "Fixation and Long-term Storage of Human Lymphocytes for Surface Market Analysis by Flow Cytometry," *Cytometry* 9: 213–219 (1988).

Primary Examiner—Douglas W. Robinson
Assistant Examiner—L. Blaine Lankford
Attorney, Agent, or Firm—Haverstock, Garrett and Roberts

[57] ABSTRACT

Cells are treated to preserve them in non-frozen hydrated form with minimal alterations to their antigens or nucleic acids. This makes the cells useful as quality control (QC) reagents for processes such as calibrating and standardizing flow cytometry equipment, for use as "unknown" test samples for QC testing programs, and to prepare patient specimens for archival storage. This method includes: (1) treating the cells to inhibit proteolysis, preferably using several protease inhibitors; (2) fixing the cells, either by contacting them with a crosslinking agent such as formalin or paraformaldehyde, or by exposure to microwave radiation, while the cells are being agitated to promote the formation of crosslinking bonds within a single cell while inhibiting the formation of cell clumps; and (3) if the cells are treated with a chemical crosslinking agent, removing the crosslinking agent and contacting the cells with a quenching agent. The cells should be stored in a solution containing protease inhibitors. This method causes little or no detectable alteration of antigenic or DNA histograms. It has been used to preserve cells that have been stored for months at room temperature, or for more than a year at refrigerated temperatures, with no substantial deterioration of surface or cytoplasmic antigens or DNA content.

13 Claims, 5 Drawing Sheets

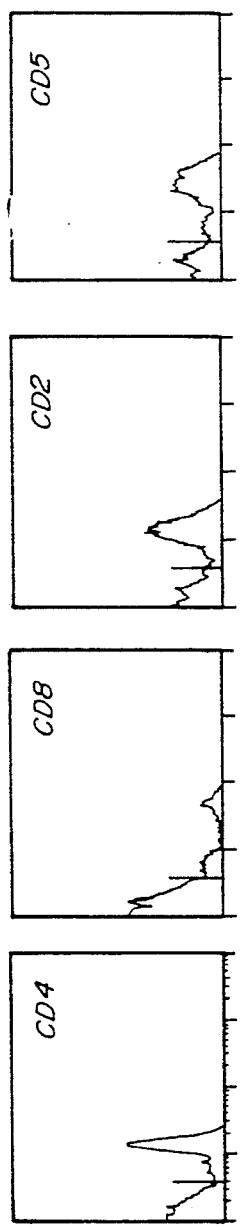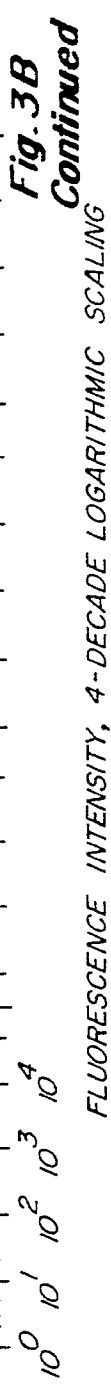

PRESERVED CELL PREPARATIONS FOR FLOW CYTOMETRY AND IMMUNOLOGY

FIELD OF THE INVENTION

This invention is in the fields of biochemistry and medicine. It provides a method of preserving cells which are biologically inert but which retain their surface antigenic proteins and DNA characteristics. Such cells are useful in flow cytometry (an automated method of analyzing cell populations) and in other immunological and analytical procedures used in medicine.

BACKGROUND OF THE INVENTION

Various efforts have been made to develop methods of preserving cells in biologically inert form, which are useful for a variety of purposes, some of which will be described below. The subject invention concerns one such method, which appears to offer a major improvement over all previous methods. Since the preserved cells provided by the method described herein are especially useful in flow cytometry, some background information on flow cytometry is provided in the following subsections.

Flow Cytometry

Flow cytometry is a method of analyzing cell subpopulations, using automated equipment. It is widely used in medical labs and in biomedical and biochemical research, and it is discussed in various books and articles such as Melamed et al 1990 (full citations are provided below) and in journals such as *Cytometry* and the *American Journal of Clinical Pathology*.

Briefly, cells entrained in a stream of liquid (such as human blood cells in buffered saline solution) are passed through a transparent tube. The tube is subjected to a beam of excitatory light having a desired wavelength. Some but not all of the cells will be fluorescent, due to a prior treatment which is carried out to distinguish certain cells from other cells.

For example, flow cytometry can be used to analyze the number or the fraction of cells which contain a certain surface protein. Since this technique involves antibody binding, the surface proteins are usually called "antigens," even though they are endogenous proteins that usually do not act as antigens in the normal sense (i.e., they do not provoke an antibody-producing response by the patient's immune system). A population of cells which are suspected of containing a certain antigen (surface protein) can be incubated with monoclonal antibodies (MoAb's) that bind only to the antigen of interest. Before being used in this manner, the MoAb's have fluorescent molecules (such as fluorescein, phycoerythrin, or rhodamine) coupled to them. If these fluorochrome-coupled monoclonal antibodies (FC-MoAb's) attach to cells having the antigen of interest, the fluorescent molecules attached to the MoAb's cause cells with those antigens to become fluorescent, while the cells which do not have those antigens do not become fluorescent.

To analyze the cells in a flow cytometer, the cells are passed through the beam of excitatory light during a test run (which may involve a research experiment, a medical diagnostic test, etc.). As they pass through the transparent tube, a light having a wavelength that excites the fluorescent molecules is shone upon them. Cells which do not have the antigen of interest, and which therefore have few or no FC-MoAb's attached to them, will have only a minimal (background) level of fluorescence; by contrast, cells which have the antigen and which have attached FC-MoAb's will emit a high level of fluorescent radiation at a different wavelength than the excitatory light. The fluorescent radiation is detected by an optical sensor, which is coupled to analytical circuitry to display and record the data.

The data generated during a flow cytometry analysis are usually displayed as a "histogram." This is a graph with fluorescence intensity (FI) on the horizontal axis. Plotted above each point along the horizintal axis is a data point which indicates the number of cells which have that particular fluorescence intensity. Two sample histograms are provided in FIG. 1, as described below.

Histograms generated by flow cytometry can provide various types of useful data, depending on the specific type of analysis being done. For example, certain types of cancerous cells have abnormally high (or low) numbers of certain proteins on their surfaces. Analysis of cells from a patient suspected of having such a cancer would generate a histogram with a normal profile if the patient does not have that type of cancer, or a histogram with a peak which is enlarged and/or shifted toward the right (or left), which would indicate that the patient has altered numbers of cells with abnormal concentrations of that surface protein. Flow cytometry can also be used to analyze the quantity of DNA in cells, using techniques described below. This also can be useful in cancer diagnosis and treatment.

Flow cytometers can evaluate very large populations of cells (millions or billions of cells). They can also be equipped with mechanical devices which shunt fluorescent cells into a separate receiving vial, which allows for isolation of only certain desired cells out of a large population of cells; this technique is referred to as cell sorting.

Quality control in Flow Cytometry

Although flow cytometry is very useful, it has been troubled by problems and limitations related to quality control (QC). Various publications such as Harvath 1988 and Caldwell et al 1987 discuss the problems encountered in trying to obtain reliable data from flow cytometry. Several government agencies and private organizations (such as the College of American Pathologists) spend substantial time and effort monitoring flow cytometry laboratories around the country, by distributing cell samples having properties known only to the testing agency, and determining whether each lab being tested can accurately evaluate the samples. This encourages labs to make sure that their flow cytometry operators have adequate training, that the MoAb or DNA staining reagents are of high quality, and that the equipment is kept running properly.

However, even with trained personnel and the best available equipment and reagents, quality control is a never-ending problem. Prior to this invention, it has been severely hampered by less-than-ideal reagents for performing QC and calibration tests.

A primary problem in flow cytometry QC is in making sure the settings on the controls (the intensity of the excitatory light, the sensitivity of the detector optics, the angular displacement between the excitatory beam and the optical detector, etc.) are calibrated and set properly for each run. It is not enough for an operator to know how to run the flow cytometer; the operator also needs to determine the proper control settings for each type of cell being tested, and for each batch of reagents being used to test cells. Different batches of any biologically active reagent can vary in their characteristics; for example, on the day they are created, different batches of MoAb's can vary in their binding affinities and in the quantity of fluorochrome molecules coupled to the antibodies. In addition, reagents undergo change and can deteriorate over time, due to processes such as fluorochrome molecules detaching from the antibodies, and non-specific aggregation of the antibodies. Also, when performing an analytical procedure, it is impossible to completely eliminate various interfering processes such as non-specific binding of antibodies or fluorochrome molecules to plastic surfaces in the pipettes, tubes, and vials used to handle the fluids. All of those variables must be accounted for somehow when an operator tests a population of cells with unknown properties.

To help an operator adjust and optimize the controls on a flow cytometer to account for such variables, it is desirable or even necessary to allow the operator to do one or more trial runs to get the flow cytometer set up and properly adjusted and calibrated before running a sample of cells that actually need to be tested. The main types of flow cytometry QC reagents used in the prior art to help an operator perform set-up and calibration involve (1) microscopic beads, or (2) lyophilized cells. A scientist usually adds a known quantity of one of those QC reagents into a fluid sample, and then analyzes the sample to see whether the intensity of the excitatory light, the sensitivity of the optical detector, the alignment of the excitatory beam and optical detector, and the other operating parameters give close to the expected results. The problem with those quality control reagents is that they can give misleading results; the more different a QC reagent is from the cells they are intended to mimic, the greater the likelihood of misleading data and suboptimal calibration.

"Lyophilized" cells, which are freeze-dried to remove all the water, are sold for use as QC reagents in flow cytometry by the Coulter Company, under the trademark "Cyto-Trol." What remains after the lyophilization process is analogous to a skeletal remnant of the cell, with weight and flow characteristics that are substantially different from living or recently treated cells. When reconstituted in water (as intended by the supplier), at least some of the lyophilized cells dissolve or break into fragments, which is undesirable. In addition, presently available "Cyto-Trol" reagents are limited to normal lymphocytes, whereas a need exists for reagents that mimic various types of abnormal cells.

Other efforts to provide QC reagents for flow cytometry have focused upon "microspheres," which are tiny beads of starch, plastic, etc., having sizes comparable to the cells being analyzed. Using microspheres for this purpose is analogous to using heavy punching bags to emulate corpses; they may weigh about the same and be roughly the same size, but their light-absorbing and light-emitting characteristics can be significantly different and potentially misleading. A number of U.S. patents invented by Abraham Schwartz and assigned to the Flow Cytometry Standards Corporation involve the use of microbeads as quality control reagents. Those patents, which include U.S. Pat. Nos. 4,857,451; 4,774,189; 4,767,206; and 4,714,682, require the use, in each experiment, of multiple sets of beads having different characteristics. This indicates that several different analyses and correlations must be performed to overcome the limitations of using beads to emulate or mimic cells during calibration operations; since the beads do not contain surface antigens, they cannot be used to perform QC testing of MoAb's.

In contrast to those prior art efforts, the subject invention provides a treated population of preserved cells, which are also referred to occasionally herein and in the literature as fixed or fixated cells. The preserved cells of this invention remain intact and hydrated throughout the fixation steps and any storage, shipping, and handling. These cells are effectively chemically inert, but they closely resemble the viable cells from which they were derived in every respect which is important to their use as QC reagents in flow cytometry. The cell proteins (both surface/external and cytoplasmic/internal) are protected in two different manners: proteolytic degradation is suppressed by chemicals that inhibit protease enzymes, and limited numbers of crosslinking bonds are used to further alter the antigenic proteins in a way which does not substantially interfere with antibody binding but which further suppresses proteolytic degradation. The crosslinking step is carefully controlled to prevent cells from crosslinking with other cells in significant quantities, which would form agglomerations that would interfere with their passage through the narrow observation tube in a flow cytometer.

In general, fixing or preserving a cell can be compared to embalming a corpse. During embalming, the blood is removed from a corpse and replaced by embalming fluids to prevent decay, but the embalmed corpse will look nearly the same and have nearly the same size and weight as the living body from which it was obtained. In a similar manner, a preserved cell will have about the same size and weight as a living cell, and if properly treated as described herein, it will retain essentially the same appearance (i.e., the same proteins and other surface molecules).

Just as importantly, this invention allows for prompt and simple preparation of QC reagents using any desired type of cell. For example, if a flow cytometry operator needs to analyze a population of B cells (a type of white blood cell), he or she can calibrate the cytometer using B cells which have been preserved by the method of this invention. If the operator subsequently wants to analyze a population of T cells (white blood cells having substantially different surface antigens), he or she can generate new settings for the cytometer by doing a calibration run using preserved T cells.

The intact preserved cells of this invention can be prepared using any cell type that is of interest, using mass-production techniques. All cell types tested to date (which includes both normal and cancerous T- and B-lymphocytes, myeloid cells, and megakaryoblasts) have been preserved with good results for prolonged periods, such as more than a year. They are stable even when not refrigerated; some cell preparations have been stored at room temperature for more than a year, and at elevated temperatures for months, with little deterioration of their antigenic characteristics or DNA content.

In addition to offering QC reagents for use in flow cytometry, the method of this invention can be used to preserve cells for various other types of immunological or other analysis. Cells preserved by the method of this invention can be analyzed using fluorescent microscopes or numerous other types of devices used in research or diagnostic labs, and they can be used as teaching aids to help doctors, students, and technicians learn how to work with and distinguish between different cell types and between normal and abnormal cells of the same type. The essential characteristic of this invention is not how the cells are used after they are preserved; it is the development of a method for preserving cells in non-frozen, hydrated form (i.e., without freezing, drying, or freeze-drying the cells) with minimal alteration of their proteins and/or nucleic acids.

One object of the subject invention is to provide a method of preserving cells in a hydrated, non-frozen manner which does not substantially alter their antigenic or nucleic acid characteristics.

Another object of the subject invention is to provide preserved cells which can be used as quality control reagents in flow cytometry.

A third object of this invention is to provide a variety of different types of preserved cells. Each type can be prepared using a selected type of cell, which can be either normal or cancerous, as the starting reagent, to provide a preserved cell preparation which closely emulates that particular type of cell.

Another object of this invention is to provide preserved cells which are intact and hydrated and which have good stability and long shelf life even when subjected to ambient or elevated temperatures.

SUMMARY OF THE INVENTION

This invention relates to a method of treating cells to preserve them in non-frozen hydrated form with minimal alterations to their surface proteins (antigens) or nucleic acids, and to cells treated by this method. This method of preservation makes the cells useful as quality control (QC) reagents for processes such as calibrating and standardizing flow cytometry equipment, and also for use as "unknown" test samples for QC testing programs. The method can also be used to prepare patient specimens for archival storage and subsequent retrospective analysis. This method includes the following steps: (1) treating the cells with protease inhibitors, preferably with a mixture of several protease inhibitors; (2) fixing the cells by contacting them to a controlled extent with a crosslinking agent such as formalin or paraformaldehyde, or exposure to microwave radiation, while the cells are being gently agitated to promote the formation of crosslinking bonds within a single cell while inhibiting the formation of crosslinking bonds between different cells; and (3) removing the crosslinking agent and contacting the cells with a quenching agent that will react with and deactivate remaining reactive groups. This method has been used to prepare metabolically inactive cells that have been stored for months at room temperature, or for more than a year at refrigerated temperatures, with no substantial deterioration of surface or cytoplasmic antigens or DNA content.

BREIF DESCRIPTION OF THE DRAWINGS

FIG. 1A contains histograms of fresh untreated lymphocytes obtained using antigenic analysis on a flow cytometer, as described in Examples 1 and 2.

FIG. 1B is a nearly identical histogram of lymphocytes taken from the same cell population after the cells were chemically preserved using the method of the subject invention.

FIG. 1C contains histograms of the same cells after 10 months of storage.

FIG. 2 is a graph showing the stability of five antigenic determinants on a population of preserved B cells over a period of nearly a year.

FIG. 3A contains histograms taken from tonsil cells which have both B-cell and T-cell antigens, the cells having been generated one day after the cells were preserved.

FIG. 3B contains histograms generated from the treated cells six weeks later.

FIG. 4A contains two histograms which indicate DNA contents of cells that were treated to make their membranes permeable, the histograms were generated using a conventional membrane treatment involving cold ethanol, followed by propidium iodide staining.

FIG. 4B is a histogram generated using cells that were chemically preserved using protease inhibitors and formalin then treated with a detergent to render the cell membranes permeable prior to propidium iodide straining.

DESCRIPTION OF THE PREFERRED EMBODIMENTS

Figure 1:
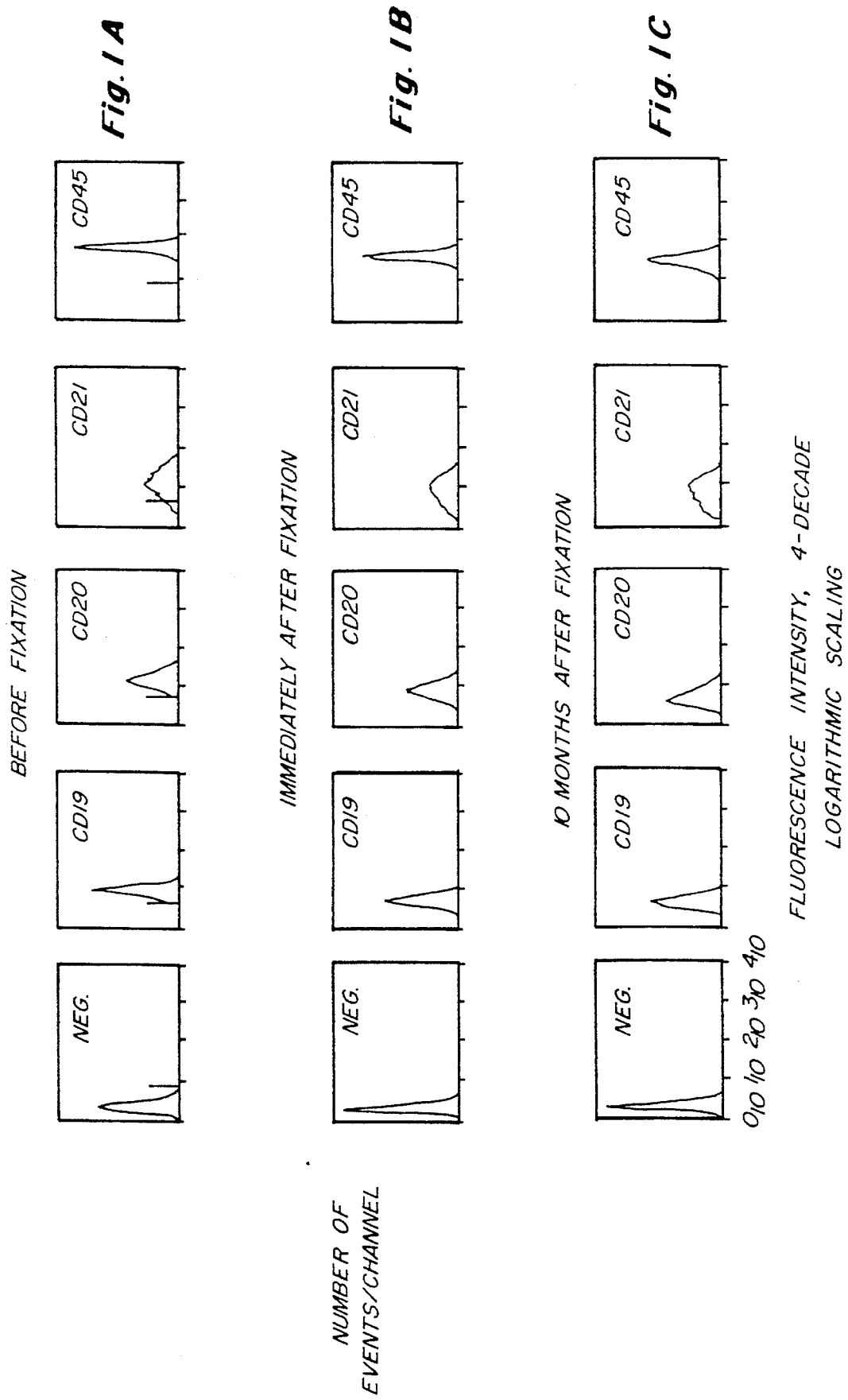

This invention relates to a method of treating cells to preserve (fix) them with limited alterations to their proteins and DNA so that the preserved cells will be biologically inert but will still display substantially the same antigenic and DNA characteristics as untreated cells. This invention also relates to cells which are preserved by the method of this invention. Such cells can be derived using any cell type as a starting reagent in order to generate preserved cells having substantially the same antigenic and DNA characteristics as fresh cells of the selected cell type. The preserved cells are useful for various purposes, such as quality control reagents for calibrating and standardizing flow cytometry equipment, and to assist and promote various other types of immunological and other cellular and medical analyses.

This method includes two steps. The first step involves treating a population of cells with at least one protease inhibitor, under conditions (concentration, temperature, and duration of exposure) which allow the protease inhibitor(s) to inhibit proteolytic and/or glycolytic activity, thereby protecting the cellular proteins from degradation by proteolytic or glycolytic enzymes, but which limit the amount of alteration of the proteins so that the ability of the treated proteins to bind to monoclonal antibodies which would bind to the unmodified proteins is not substantially altered. This protease inhibition step is described in greater detail below.

In the second step, which involves molecular crosslinking and which is referred to herein as the fixation step, the cells are contacted with a suitable crosslinking agent such as formalin or paraformaldehyde. Preferably, this is done while the cells are being gently agitated, to promote the formation of bonds within a single molecule or cell rather than crosslinking bonds between different cells. During this step, the conditions of concentration, temperature, and duration of exposure are controlled to generate an effective amount of crosslinking to render the cells biologically inert without severely altering their protein binding or DNA staining characteristics. At the end of the fixation step, the crosslinking agent is substantially removed, diluted, or inactivated, and the cells are contacted with a "quenching" agent that will react with and deactivate any remaining reactive groups. In all steps, the protease inhibitors are present.

In an alternate preferred embodiment which is faster and easier to carry out, the fixation step can be carried out by heating the cells using microwave radiation. This can be done in the presence of a quenching agent such as a protein in a tissue culture medium.

After the protease inhibition and fixation steps are completed, the cells can be stored, shipped, and handled in intact, hydrated form, usually without requiring refrigeration. Preferably, they should be maintained in a solution that contains protease inhibitors.

These treatment steps are performed on a "population" of cells. As used herein, a population of cells refers to a culture of cells, or to any large number of cells (such as more than a thousand cells), regardless of what type of treatment they may have been subjected to immediately before the treatment method of this invention. For example, the method of this invention can be used on cells which have previously been frozen or stored in a refrigerator, or on cells directly obtained from a patient without going through a culturing step to increase the numbers of cells. The cells can be human cells, other types of mammalian cells, cells of other animals used in lab research, bacterial cells, etc. The cells should be in a liquid suspension to make them suitable for use as described herein. This inherently includes blood cells and blood cell precursors; it can also include cells derived from cohesive tissue if steps are taken to separate the cells into a single-cell suspension, as described below.

Typically, to prepare cells for use as QC reagents in flow cytometry, the cells are cultured in a suitable nutrient medium, using reagents and methods known to those skilled in the art. Example 1 describes a typical human cell culture protocol, which involves culturing lymphocytes in RPMI 1640 medium (which includes fetal bovine serum) and antibiotics, in an agitated vessel such as a spinner flask to prevent the cells from clumping together. Preferably, an immortal cell line is used, which can be obtained from a cancer patient having a disease such as leukemia or lymphoma. Immortal cell lines can also be generated by using a virus such as Epstein-Barr virus to transform a cell strain (which normally can reproduce only a finite number of times) into an immortal cell line (which can reproduce an unlimited number of times). A great deal of research is being done on cell aging and senescence, and it may be possible in the future to induce cell strains to divide any number of times if certain growth factors are added to the culture medium; accordingly, any such culture techniques or reagents now known or subsequently discovered can be used to culture the cells.

If desired, the cells can be subjected to any type of therapeutic or experimental treatment before commencing the preservation method of the subject invention. For example, a great deal of toxicological research is being done with known or suspected carcinogens, mutagens, teratogens, and growth factors. A cell population (which can be altered compared to a natural population, using genetic engineering or random mutagenesis) can be treated with any known or experimental drug, hormone, or toxin, cultured for a suitable period to allow the manifestation of any alterations in the cells, and then preserved using the method of this invention.

The cells are grown in suspension until they reach a suitable cell density, which will depend on the specific type of cell being used; typical preferred densities usually range from about $5\times10^5$ to about $5\times10^6$ cells/ml. If appropriate densities are used, more than about 95% of the cells harvested from the solution are viable.

The cell suspension is centrifuged at a relatively slow speed (such as about 150 to about 400 G's), to condense them into a pellet. The supernatant nutrient medium is removed, and the cells are washed (preferably several times) in a protein-free phosphate buffered saline (PBS) solution containing one or more protease inhibitors (PI's).

In general, proteases (also called proteinases, or proteolytic enzymes) are enzymes that break down protein molecules into smaller polypeptides or into amino acids, by breaking the peptide bonds between adjacent amino acids. Trypsin, chymotrypsin, pepsin, carboxypeptidase, elastase, thrombin, and collagenase are examples of proteases. Proteolytic activity is a natural and continuous function in any viable cell; it is part of the cycle by which old, damaged, or inactivated proteins are broken down into their building blocks; the building blocks are then used to make new protein.

In general, protease inhibition is usually done in either of two manners: (1) by inactivating protease enzymes, such as by using compounds such as diidopropylphosphofluoridate (DIFP), or (2) by chemically altering protein molecules so that they are less susceptible to proteolytic cleavage. It should be noted that any reagent which chemically modifies all proteins in a non-specific manner will tend to inactive protease enzymes, since protease enzymes are themselves proteins.

Some non-specific protease inhibitors are relatively small chemically reactive molecules (much smaller than antibodies) which react with pendant groups on the proteins (such as alkyl, carboxyl, and/or amine groups). Many types of PI molecules donate hindering groups or crosslinking structures to the proteins, thereby inhibiting the ability of protease enzymes to reach and break the peptide bonds. Such hindering groups and crosslinking bonds are added to the proteins on a presumably random and scattered basis. If the concentration of the PI agents is suitably limited, and if the temperature and duration of the protease inhibition period(s) are also suitably limited, this treatment step can inhibit protease activity while leaving the altered polypeptides susceptible to normal binding by antibodies.

It should also be noted that non-specific PI's also tend to exert toxic effects on various other organelles (such as the mitochondria) inside a cell. These effects bring the normal metabolic processes of the cell to a halt, further impeding proteolysis.

The suitable limitations for the PI agents depend on the specific reaction mechanism and reactivity of the PI agent(s) used, the quantity and concentration of each PI agent added to the cells, the temperature of the reaction, the duration of each PI incubation step, and the number of PI incubation reactions used. It is preferable to conduct a PI reaction as a multistep process, in which a first batch of PI agents is reacted with the cells, then rinsed away, and then a second batch of fresh PI agents is added to the cells so the PI reaction can be repeated. Suitable reaction conditions which work effectively with a wide variety of cells are described in the examples. These conditions can be modified and assessed for any protease inhibiting agent or mixture of agents under any modified conditions, using routine experimentation in light of the procedures described below, to assess whether such agents or modified reaction conditions lead to satisfactory results in preserving any specific type of cell.

Preferably, a mixture of several PI agents should be used which involve different protease inhibiting mechanisms, to ensure complete, thorough, and relatively rapid protease inhibition. One suitable mixture comprises three PI's, which are sodium azide, phenylmethylsulfonylfluoride (PMSF), and ethylenediaminetetraacetate (EDTA), and a sulfhydryl-containing molecule which serves as a stabilizing agent, such as dithiothreitol (DTT). That four-component mixture, in phosphate buffered saline (PBS) solution, is referred to herein as the PI mixture. The PI mixture remains in contact with the cells throughout all of the treatment steps (including the fixation step) and preferably should be present in the suspension medium used to store the cells.

Numerous other PI agents are known, many of which are good candidates for use in the subject invention. Such agents include 4-(amidinophenyl)methanesulfonyl fluoride, aprotinin, antipain, antithrombin III, alpha-1-antitrypsin, aprotinin, bestatin, calpain inhibitor, chymostatin, 3,4-dichloroisocoumarin, elastatinal, kallikrein inhibitor, leupeptin, alpha-2-macroglobulin, pepstatin, phophoramidon, N-tosyl-L- lysine chloromethyl ketone, and N-tosyl-L-phenylalanine chloromethyl ketone. Any of these compounds, or various other compounds known to function as protease inhibitors, can be tested for suitability for preservative use with any specific type of cell according to the methods described herein, using routine experimentation. In a similar manner, various other compounds other than DTT can be used as stabilizing agents; two such compounds which contain sulfhydryl groups include 2-mercaptoethanol and cysteine.

In each initial treatment step using the above-identified PI mixture (sodium azide, PMSF, EDTA, and DTT in PBS), a pellet of cells is mixed with and suspended in the PI solution, using any suitable method of agitation such as a stirring or vortex device. The PI mixture is allowed to react with the cells for a suitable time, such as about 5 to 10 minutes, at a suitable temperature, preferably less than room temperature. About 4° C. is a convenient temperature, since it is the storage temperature maintained in most conventional refrigerators. The unreacted PI reagents are then removed by centrifuging the cells at low speed to form a pellet and discarding the supernatant, then the cycle preferably is repeated at least once.

In one preferred method that has been found to be highly effective without requiring a great deal of time or tedium, the cells are washed in the PI mixture three times. However, the number of cell washings can be increased or decreased without losing the desired effect, particularly if the incubation times and temperatures are adjusted accordingly. For example, two washings probably would be adequate for treating most cell types if the PI mixture remained in contact with the cells for a sufficient period of time, especially if the incubation temperature is raised above 4° C.

After the initial PI treatment cycles are completed, the cells are resuspended in cold PBS containing the four PI reagents, then the cells are mixed with a large excess (such as about a 50-fold excess, on a volume-to-volume (v/v) basis) of a suitable crosslinking agent. The cell suspension is incubated under suitable conditions (such as about two to four hours at room temperature) while being gently but constantly agitated. A rocker platform is preferred for the gentle agitation; however, various types of stirring devices might also be suitable, particularly if a large stirring paddle rather than a single stirring rod is used to minimize unstirred zones in the reaction vessel.

One class of preferred crosslinking preservative agents comprises relatively small aldehyde molecules, such as formalin, which is a solution of 40% w/v formaldehyde in water, which usually contains some methanol as a byproduct of formaldehyde reduction. The formaldehyde molecule, $CH_2O$, has the following structure:

As described in various texts which address the fixation and preservation of cells (see, e.g., Feldman and Dapson 1980), this highly reactive molecule undergoes a series of non-specific reactions which result in a methylene bond that crosslinks any two molecules that happen to be in sufficiently close proximity. The first reaction in this step involves a non-specific reaction with any type of molecular group having an exposed hydrogen atom, such as a lysine or glutamine residue (or any other residue having an amine, sulfhydryl, carboxyl, or aromatic hydrocarbon group) on a protein. In this reaction, the formaldehyde group is converted into a hydroxyl group when the hydrogen atom from the substrate shifts to the oxygen on the formaldehyde, as follows:

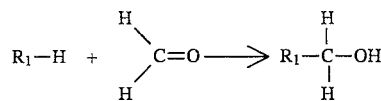

In the second reaction, the hydroxyl group reacts with a second exposed hydrogen atom, which can belong to a nearby residue in the same protein molecule, or to a nearby protein molecule. In this reaction, the second hydrogen atom reacts with the hydroxyl group from the crosslinking agent, to form a molecule of water which dissociates from the newly formed molecular complex, leaving behind a crosslinked molecular complex having a methylene ($CH_2$) bridge, as follows:

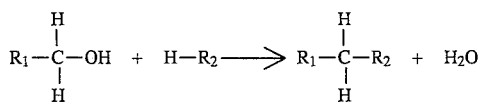

The formation of a network of randomly placed crosslinking bridges, under conditions of gentle but constant agitation and using a relatively small crosslinking agent, promotes the formation of intramolecular and intermolecular bonds within a single cell, and often within a single molecule (such as a single protein molecule). This effectively fixes and maintains the treated protein molecules in configurations which closely resemble their original configurations, thereby preserving and protecting, to a large extent, their ability to bind to monoclonal antibodies that react with the native proteins. At the same time, the use of a small crosslinking agent in conjunction with gentle agitation of the cells inhibits the formation of crosslinking bonds between different cells; this prevents the formation of cell clusters that might clog the very small diameter tubes used in flow cytometers.

A preferred crosslinking agent for use as described herein comprises a somewhat diluted aqueous solution of formaldehyde, such as formalin (the common name given to a solution of 40% formaldehyde in water). Several other crosslinking agents have also been shown to work effectively for the purpose described herein, including paraformaldehyde and a mixture referred to as PLP (paraformaldehyde, lysine, and periodate). These agents, although suitable, tend to be more expensive and more difficult or tedious to work with. Paraformaldehyde normally must be synthesized shortly before use, since it is relatively unstable. By contrast, formalin is easily available, relatively inexpensive, and relatively stable when properly packaged and stored, and has been shown to be suitable for all types of cells tested to date.

Most of the chemical crosslinking agents tested to date involve aldehyde groups, since they work quite effectively and are relatively inexpensive. It is possible that for some types of cells, other types of crosslinking agents might be suitable or even preferable. Any compound which is known to be a crosslinking agent can be tested as described herein using routine experimentation and can be used if found to be suitable. However, it should be noted that various types of crosslinking agents have been tested which did not work effectively with the cell types tested under the conditions used in those particular experiments. Such agents, which do not appear to be suitable based solely on the limited tests done to date, include:

1. glutaraldehyde, which can induce undesired autofluorescence in the cells being treated; and, 2. methanol and ethanol, which tend to cause cells to form cell clusters that can foul flow cytometry equipment, and can cause loss of some antigens.

In addition, it is also presumed that crosslinking agents which contain heavy metal, such as Zenkers' agent and Bouin's agent, would be less preferred than aldehyde crosslinking agents, for several reasons. They tend to be more expensive than formalin, they tend to degrade antigens on the surfaces of cells being analyzed, and the disposal of used reagents containing heavy metals generates toxic waste problems and additional expense.

In general, a crosslinking agent is suitable for use as described herein if it satisfies the following criteria:

1. if the cells are intended for use in tests involving analysis of antigens, the crosslinking agent should not degrade the antigens or severely impede their affinity for monoclonal antibodies which bind to the untreated antigens;

2. if the cells are intended for use in tests involving analysis of DNA, the crosslinking agent should not degrade DNA inside the cells or prevent fluorochrome reagents such as propidium iodide from binding to DNA;

3. the crosslinking agent should not generate undesired fluorescence, and should not cause the cells to form cell clusters.

After the crosslinking step has been completed using a suitable agent, the crosslinking agent preferably should be removed by centrifuging the cells at a relatively low speed, discarding the supernatant, and washing the cells, preferably at least twice, in PBS solution containing the PI mixture. Some portion of the crosslinking agent can remain in contact with the cells, provided that it is adequately diluted and/or inactivated by a quenching agent.

In general, "quenching agents" are compounds used to inactivate reactive molecules and terminate a reaction. Glycine, gelatin, albumin, and serum proteins have all been tested as quenching agents, and all work suitably. Other suitable quenching agents can be determined using routine experimentation; any free amino acid, protein, or other molecule containing amine groups is a good candidate for use as a quenching agent to prevent additional crosslinking due to residual reactive groups after the crosslinking agent has been removed.

At the end of the crosslinking and quenching steps, the treated cells will be suspended in PBS, preferably containing the PI mixture, preferably at a relatively high concentration such as about $10^7$ cells/ml. If desired, an additional substance such as gelatin or bovine serum can be added to the suspension, to make the cells easier to manipulate and to reduce non-specific adherence to plastic surfaces.

These steps have been be used to prepare metabolically inactive B cell lymphocytes that have been stored for up to three months at room temperature, or for more than a year at refrigerated temperatures. After being stored for those prolonged periods, the cells have been used as QC reagents in flow cytometry with completely satisfactory results.

The methods of this invention have also been used to treat various other types of cells, including cells from various lymphohematopoietic lineages as described in Example 6. With a few limitations, the cells were fixed in intact form without substantial alteration to their antigens; they were stored for prolonged periods and served effectively as QC reagents.

As described in Example 6, various modifications can be made to optimize the preservation protocol for certain types of cells. For example, it was found that T-cell antigens tended to have better affinity for monoclonal antibodies if the formalin crosslinking step was reduced from the normal 3-hour period (used for B cells) to 1.5 hours. In addition, since non-lymphoid malignant cells tend to contain high quantities of hydrolytic enzymes capable of degrading surface antigens, the concentration of protease inhibitors in the PI solutions was doubled. If any particular cell type shows itself to be resistant to preservation using the standard methods described herein, various modifications such as described above can be tested for the treatment of any such cell type; in addition, such cells can be tested to determine whether they can be preserved effectively using microwave radiation rather than a chemical crosslinking agent, as described below.

This method can be performed on any cell type that is of interest in flow cytometry, to provide QC reagents for use in analyzing those same types of cells. For example, QC reagents generated by preserving B cells can be used to calibrate a flow cytometer prior to testing B cells obtained from a patient, and QC reagents generated from T cells can be used to calibrate a flow cytometer prior to testing T cells.

As QC reagents, the preserved cells can be used to assess the characteristics of other reagents such as fluorescent monoclonal antibodies immediately before those reagents are used in a test. The QC reagents of this invention can also be used by groups such as the College of American Pathologists, to assess the reliability of labs and clinics which provide flow cytometry services, and to provide materials for continuing education programs in flow cytometry.

The method of this invention can also be used to preserve cells for various other types of immunological or other analysis. For example, cells preserved by the method of this invention can be analyzed using fluorescent microscopes or numerous other types of devices used in research or diagnostic labs. In general, the subject invention relates to a method of preserving cells, and to cells which have been preserved by this method; it is not limited to specific ways of using the cells after they have been preserved. Indeed, the availability of highly stable, non-frozen, hydrated preserved cells is likely to stimulate a variety of new uses, some of which cannot be anticipated today.

Since flow cytometry is performed by passing a liquid suspension of cells through a tube with a very small diameter, it is used primarily on cells which normally grow in suspension, such as bacteria cells, or lymphohematopoietic cells from humans (i.e., blood cells and lymphocytes). However, if desired, it is also possible to treat a sample of cohesive tissue using certain substrate-specific proteolytic enzymes such as collagenase to digest the proteins that hold anchorage-dependent cells together. This causes the still-viable cells to dissociate from each other, forming a suspension of cells. The suspended cells can then be treated as described herein.

There are also a number of variations in the procedures used to conduct flow cytometry which can be adapted to cells that have been preserved using the methods of this invention. For example, "indirect" antigen analysis involves the use of two different antibody preparations. The first antibody is a MoAb which is not coupled to a fluorochrome molecule; it is incubated with the cells, and binds to the cells if the antigen is present. Unbound MoAb's are then removed by washing the cell suspension, then the cells are incubated with a second type of antibody (either monoclonal or polyclonal) which is coupled to a fluorochrome molecule, which binds to the first antibody. Such indirect or double-antibody techniques can be used with cells that have been preserved as described herein.

In another significant variation that is commonly used in flow cytometry, two or more types of antigens can be analyzed during a single run. This can be done by using two different monoclonal antibodies, each of which binds to a different antigen. Each type of antibody is coupled to a different type of fluorescent molecule. For example, one antibody can be coupled to fluorescein isothiocyanate (FITC), which emits fluorescent light with a peak wavelength of about 515 nm (green) when excited by a light having a wavelength of about 488 nm; the other antibody can be coupled to R-phycoerythrin, which emits light having a broader wavelength in the orange and red region when excited by the same excitatory light. The intensities of both fluorescent emissions can be analyzed separately by using two optical sensors with different wavelength filters, to separately indicate the concentration of each type of antigen on the cells. This type of analysis is often referred to as "dual color" analysis. As described in Example 4, dual color analysis has been used successfully with cells that were preserved as described herein.

This invention also relates to a method for calibrating a flow cytometer. Shortly before using the flow cytometer, cells of the selected cell type which have been treated as described above are contacted with fluorochrome-coupled monoclonal antibodies (or with DNA-staining chemicals, as described below). Treated cells with any bound antibodies are then passed through a flow cytometer, using the normal analytical procedures wherein an excitatory light is shone on the cells while the cells are passing through the instrument. While the cells are passing through the machine, the optical detector(s) in the flow cytometer detect the quantity of flourescent radiation emitted by the cells. The optical detector is positioned in a first alignment, and an electronic signal generated by the optical detector is processed by an data presentation circuit in the flow cytometer based on initial control and amplification settings. The data generated at that alignment and control settings can be used in either or both of two ways: (1) it can be used to adjust the detector alignment and control settings in the instrument, to give an optimal data display (e.g., to group the data points into the tightest cluster that can be achieved in a histogram); and, (2) it can be used to establish baseline values which will indicate the quality, affinity, fluorescence levels, and other characteristics of the fluorochrome-coupled monoclonal antibodies or other reagents being used on that aprticular day, immediately before those same reagents are used to analyze a sample of non-preserved cells have unknown characteristics.

This invention also relates to a composition of matter, comprising a population of human cells which have been treated by protease inhibitors in a manner which has rendered the cells metabolically inert and which has inactivated proteolytic enzymes in the cells without substantially altering the binding characteristics of the cellular proteins to monoclonal antibodies having affinity for cellular proteins of untreated cells of the same type, wherein the cells are stored in hydrated form in saline solution containing at least one protease inhibitor. Such preparations can be mass-manufactured using automated equipment to achieve high standards of uniformity and predictabiligy. They can be bottled or packaged in any other desired manner and in any desired quantity, stored for prolonged periods, and sold and shipped to medical and diagnostic clinics, hospitals, and other locations that use flow cytometry.

Cell Preservation Using Microwave Radiation

An alternate preferred embodiment of this invention uses microwave radiation instead of a chemical crosslinking agent such as formalin as a fixation means.

Microwave radiation has previously been used to fix cohesive tissue samples for histological analysis under a microscope; see, e.g., Leong 1988. That technology usually involves radiation to fix the tissue, embedding the fixed solid piece of tissue in a block of paraffin, then using a microtome to slice the tissue into very thin sections for direct analysis under a microscope. To the best of the Applicant's knowledge, microwave radiation has never been previously used to fix or preserve suspension cells for flow cytometry analysis.

As described in Example 7, cells were grown in suspension culture and treated with the PI solution. Instead of contacting the PI-treated cells with formalin, the cells were treated with microwave radiation instead. No formalin was used at any time during the preservation of these cells.

The cells were irradiated in the following manner. They were suspended in tissue culture medium (which contains a small quantity of protein from fetal calf serum). The three PI reagents (sodium azide, PMSF, and EDTA) and the DTT stabilizer were added to the suspension to obtain the same final concentrations specified in Example 1. The cell suspension was divided into aliquots containing 1 to 5 mL each, which were placed in plastic tubes. A single cube with no cap or stopper was placed in a beaker containing distilled water at room temperature. The beaker was placed on a rotary table inside a microwave oven equipped with a shut-off switch that could be actuated by a temperature probe. The oven was turned on at full power, and the beaker and cell suspension were irradiated until the temperature of the water surrounding the cells reached 70° C., at which time the temperature probe shut off the oven. The plastic tube holding the cells was promptly removed from the hot water, cooled by immersing it partially into a beaker of cold tap water, then placed inside a refrigerator maintained at 4° C. No quenching agent was added after the microwave radiation; the protein in the culture medium presumably served as a quenching agent. Cell samples were tested shortly thereafter, and again several weeks later, using the immunostaining and flow cytometric analyses described in Example 2. The histograms generated by those tests indicated that the microwave radiation treatment in combination with the protease inhibitors effectively preserved the cells without substantial alteration of the antigens on the cell surfaces. Since there was no serious deterioration of the molecules on the cell surface, and since the temperatures in the cells did not exceed 70° C., it is presumed that there was no substantial deterioration of cytoplasmic antigens or cellular DNA.

Analysis of DNA and Cytoplasmic Antigens

Flow cytometry can also be used to analyze molecules inside cells, such as DNA and cytoplasmic antigens. In general, such anmalysis involves treating the cells with agents that render the cell membranes permeable, then contacting the cells with either (1) fluorochrome-coupled monoclonal antibodies that bind to cytoplasmic proteins, or (2) stains such as propidium iodide which interact with DNA. The standard techniques used for MoAb analysis of cytoplasmic antigens are described in Schroff et al 1984; those techniques can be adapted for use on cells that have been treated and preserved as described herein.

The quantity of DNA in cells can provide useful data in determining whether a patient has cancer, and in selecting the best course of treatment, as follows. Cells generally go through several phases during their mitotic (cell-splitting) cycle. During the G0 and G1 phases, most human cells contain a normal complement of 46 chromosomes (two copies of each of the 23 chromosomes). During the G1 phase and even more strongly during the S phase, additional DNA is synthesized, until a cell reaches the G2 phase, when it is almost ready to divide, and the M phase, during which actual mitosis (division) is taking place. During the G2 phase and at the start of the M phase, the cell contains a quantity of DNA roughly equivalent to 92 chromosomes. It divides soon thereafter, to form two cells which have 46 chromosomes each, to start the cycle again.

In various types of cancer diagnoses, it is very useful to know what percentage of cells are in each of the phases. For example, if a breast cancer patient has a high proportion of cells in the S or G2 phases, the tumor is relatively aggressive and needs aggressive treatment. By contrast, if a breast cancer patient has a relatively low number of cells in the S and G2 phases and the large majority of cells are in the G0 and G1 phases, the treatment can be less severe and will have fewer adverse side effects. In addition, cancerous cells often are "aneuploid" and do not contain the proper number of chromosomes; they can have either too few or too many, and thus will have abnormal DNA content.

Flow cytometry can be used to assess the fractions of cells in those various phases, and the fraction of cells that are aneuploid. The cells are first treated with detergents which render the cell membranes permeable so that other agents can enter the cell interiors. The cells are then mixed with a compound such as propidium iodide, a fluorescent molecule which has an affinity for the molecular gaps between the bases in DNA. Since propidium iodide also has an affinity for double-stranded RNA, which exists in ribosomal RNA and transfer RNA, the cells are usually treated with an RNAse enzyme to degrade the RNA in the cells.

After a suitable incubation period which allows the propidium iodide stain to bind to DNA, the cells are run through a flow cytometer, and the intensity of the fluorescent emission indicates the quantity of DNA in the cell. Usually, it is not necessary to rinse away excess propidium iodide; because of quantum dynamic factors that do not require attention here, the degree of fluorescence increases dramatically if propidium iodide molecules align with each other in parallel planes, which occurs when they move into the gaps between the bases in double stranded DNA.

When the quantity of DNA in cells from a patient suspected of having a leukemia or lymphoma is being analyzed, there will be a large peak (indicating a large number of cells) at a fluorescence intensity which can be given an intensity designation of 100. Those are the "resting" cells in the G0 and G1 phases. There will be a second smaller peak at a fluorescence intensity of 200, which indicates the number of cells in the G2 and M phases. If the cell population is healthy and non-cancerous, there will be relatively few cells in the region between the G0/G1 peak and the G2/M peak. In other words, there will be relatively few cells in the S phase where DNA is being actively synthesized, because the S phase normally does not last very long, and not very many cells are in that phase at a given time in a healthy patient. However, if a patient has cancer, there will be a larger number of cells distributed between the two peaks, forming a plateau or a mound on the histogram. The shape and size of that plateau or mound between the two peaks can give a physician helpful information in planning the best course of treatment for the patient.

Figure 4B:
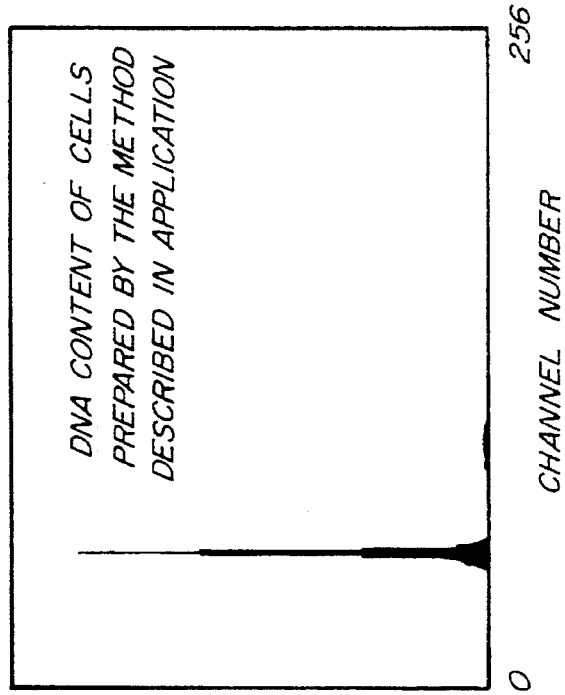

As described in Example 8 and as shown in FIG. 4, the reagents and methods of this invention have been used to preserve cells for DNA analysis with good results. The cell preservation procedure was performed as described above and in Example 1. After all of the protease inhibition and formalin crosslinking steps were completed and the cells were resuspended in the PI solution, a membrane-modifying detergent was added to the suspension. After about 30 minutes, the cells were either stained with propidium iodide and analyzed in a flow cytometer, or refrigerated at 4° C. for up to a full year before staining and analysis. The resulting histograms, taken (1) shortly after preservation and (2) after prolonged storage, indicated that the cell preparation methods worked properly and the preserved cells were highly stable despite having permeable membranes. Those cells could be used as effective QC reagents a year or more after preparation.

EXAMPLES

Example 1

Preservation of Human B-cells

Cell from the human B-cell line RPMI 1788 (American Type Culture Collection, Bethesda, Md.) were grown in liquid suspension culture in RPMI 1640 tissue culture medium for approximately 4 days. These cells were then harvested after reaching a cell density of $1.5 \times 10^6$ cells/mL. The total volume of cultured cell suspension (2 liters) was pelleted by gentle centrifugation (150 g for 15 minutes) in multiple polypropylene screw-top bottles, each of 250 mL capacity. The cell pellets were then pooled and washed 3 times in a mixture referred to herein as the "protease inhibitor" (PI) solution. This mixture was protein-free phosphate buffered saline (PBS; pH 7.4) containing three protease inhibitors (sodium azide, phenylmethylsulfonylfluoride (PMSF), and a tri-potassium salt of ethylene diamine tetraacetate (EDTA)), as well as a stabilizer, dithiothreitol (DTT). The final concentrations of those four chemicals in the PI solution were sodium azide, 0.01% w/v; PMSF, 200 uM; tri-potassium EDTA, 400 uM; and DTT, 400 uM. All four chemicals and the PBS solution were obtained from Sigma Chemical Company, St. Louis, Mo.

Cells were resuspended at a concentration of $10^8$ cells/mL in the PI solution. Ten mL of this cell suspension was slowly added to a fifty-fold (v/v) excess of 2.5% buffered formalin in the PI solution. The mixture was gently agitated on a rocker platform at room temperature for 3 hours. The mixture was pelleted by centrifugation, and the cell pellets were washed 3 times in the PI solution and resuspended in the PI at $10^8$ cells/mL. Glycine (Sigma Chemical, Co., St. Louis, Mo.) was added to a final concentration of 100 ug/L. After further incubation of 1 hour at ambient temperature on a rocker platform, 0.05% (w/v) gelatin was added, and the cells were aliquoted into 50 mL polypropylene tubes at a concentration of $10^7$ cells/mL for storage at either 4° C. or 25° C.

Example 2

Immunostaining And Flow Cytometric Analysis of the Preserved Human B-Cells

Preserved human B cells prepared as described above were divided into 50 uL aliquots containing about $5 \times 10^5$ preserved cells each. They were immunostained by addition of fluorescently tagged MoAb's using standard techniques for immunostaining lymphoid cells (see, e.g., Caldwell et al 1987). An aliquot of 50 uL of optimally diluted MoAb's was added to a 50 uL aliquot of the preserved cell suspension; the mixture was incubated at 4° C. or at room temperature for 30 minutes, washed thrice in PBS, and analyzed as described below.

The specific monoclonal antibodies used included CD19 (Leu 12), CD20 (Leu 16), CD21 (B2), CD45 (HLe-1), and HLA-DR, as well as an isotypic negative control MoAb. The Leu 12, Leu 16, HLe-1, HLA-DR, and isotypic negative control antibodies were purchased from Becton Dickinson, Mountain View, Calif. The B2 antibody was from Coulter Immunology, Hialeah, Fla. All MoAbs had been directly conjugated to fluorescein isothiocyanate (FITC) by the supplier.

Each immunostained preserved cell preparation was analyzed by flow cytometry in the same manner that would be normally used to examine of fresh lymphoid cells (see, e.g., Caldwell et al 1987). Light scatter histograms of orthogonal light scatter versus forward angle light scatter were used to electronically identify the cells. A Profile flow cytometer (Coulter Electronics, Hialeah, Fla.) or a FACScan flow cytometer (Becton-Dickinson, Mountain View, Calif.) was programmed to collect fluorescence histograms from a minimum of 10,000 preserved cells from within the light scatter gates.

From these histograms, the percentage of cells positive and negative for each MoAb, as well as the standardized fluorescence intensity (FI), were determined with the aid of computer software (Coulter or Becton Dickinson). In order to monitor FI, it was necessary to standardize the instrument settings, using fluorescent beads. The optical alignment was adjusted using "Full-Bright" beads, and the fluorescence intensity settings were adjusted using "2% Bright" beads (both from Coulter Electronics). The instrument and beads were used as described in Caldwell et al 1987.

FIG. 1 illustrates the fluorescence histograms of the immunostained B-cells at three different times. The top row displays the results of cytometric analysis done before cell preservation; this row displays the baseline data gathered prior to any alteration of the cellular antigens. The middle row contains data gathered immediately after preservation; the results are very similar, which indicates that the processing described in Example 1 did not seriously degrade the antigens on the cell surfaces. The bottom row shows that similar results were obtained after the treated cells had been stored for 10 months at 4° C.; this indicates that the cells and cellular antigens, after being treated as described above, are stable over a prolonged period of time.

Example 3

Studies of Stability of Preserved Human B-Cells

Figure 2:
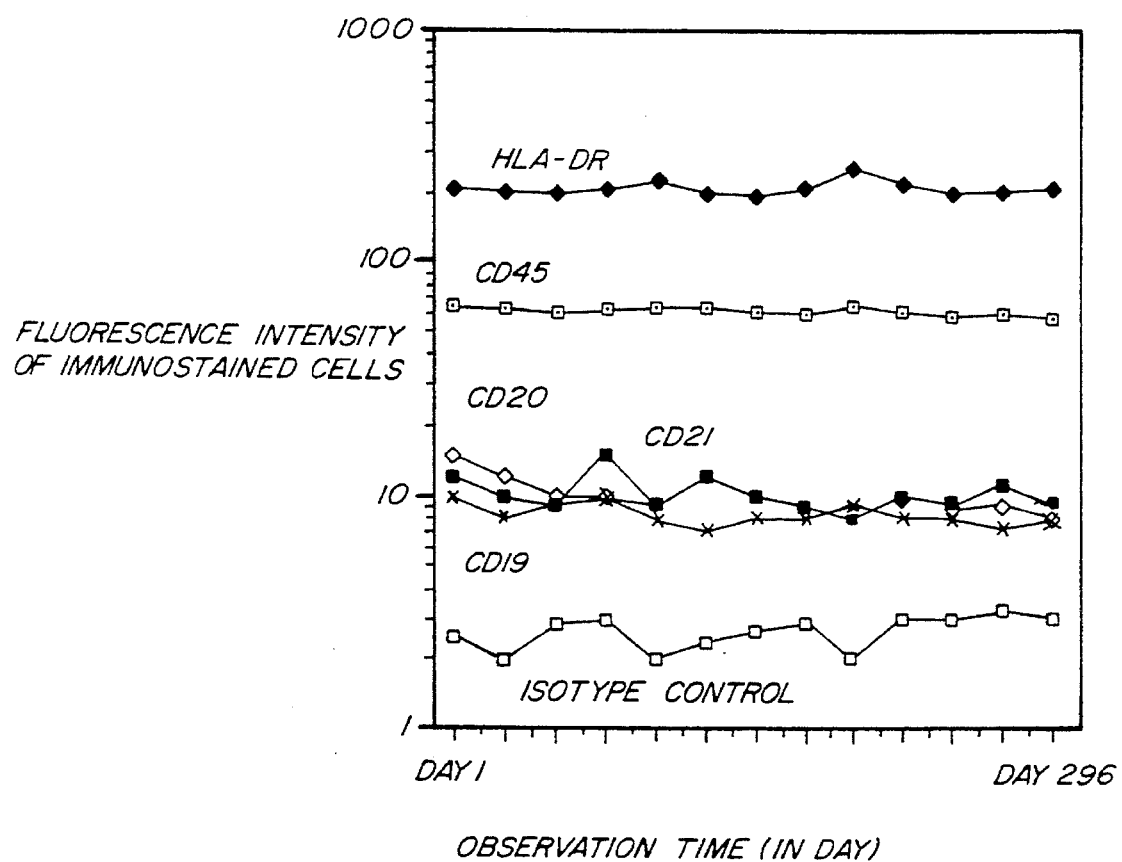

In order for preserved cells to be useful as quality control reagents, they must maintain a defined level of MoAb positivity and antigenic and light scatter stability. Therefore, specific lot numbers of preserved cells were tested for their time-dependent immunoreactivity as defined by MoAb positivity and fluorescence intensity, by evaluating the reactivity of the preserved cells (stored at 4° C. in the PI solution described in Example 1) periodically for more than a year. These tests used several different tagged antibodies; each type of antibody reacted with a different type of antigen. The results of these tests are displayed in FIG. 2. All antigens showed very good stability.

Because reagents being shipped across large distances and handled in occasionally unpredictable manners can be subjected to fluctuations in temperature, additional tests of shelf life were performed on samples stored at room temperature for a year or at 37° C. for 3 months. The results were all satisfactory and indicated good shelf life of the preserved cells even when not refrigerated.

Example 4

Use of Preserved Human B-Cells for Dual-Color Compensation

Dual-parameter staining of preserved cells with combinations of MoAbs labelled with different types of fluorescent labelling molecules may be used for color compensation adjustments on flow cytometers. Such reagents are useful when it is desirable to simultaneously determine the presence of 2 surface antigens. For example, FITC (which emits at a green wavelength) can be attached to one MoAb which will bind to one type of antigen, while phycoerythrin (PE, which emits at a broader band of wavelengths including red) can be coupled to a different type of MoAb which binds to a different antigen. Both fluorescent molecules can be excited by a single wavelength, and they can be measured independently to determine the quantity of each type of labelled antibody bound to preserved cells. Such dual-color preserved cells can be used for various purposes, such as calibration reagents to allow the necessary instrument adjustments to implement correct color compensation prior to dual-color analysis of an unknown population of cells.

To carry out such a test, human B-cells were preserved as described above. For immunostaining, a FITC-labelled MoAb was added first (as described above), followed 5 minutes later by addition of PE-labelled MoAbs which bound to a different antigen. After incubation, the preserved cell preparation was examined by flow cytometer for the presence of green (FITC) and red (PE) fluorescence. Dual-color immunostaining treatments were performed periodically over a space of 18 months, followed by flow cytometry analysis shortly after immunostaining. These tests confirmed that the cellular antigens were stable for at least 18 months.

Example 5

Fixation and Examination of Human Tonsillar T- and B-cells

In certain lymphoid tissues such as tonsil, both T-cell and B-cell antigens are present on the subpopulations of T-cells and B-cells. Cells obtained from human tonsil were chemically preserved as described in Example 1; the only exception was that fresh uncultured cells were used, and the incubation in 2.5% formalin was reduced to 1.5 hrs. The method of immunostaining and flow cytometric analysis was as described above in Example 2, except that MoAbs were used that identified not only B-cell antigens (CD-19, CD-20, CD-45, and HLA-DR), but also antigens found on T-cells and T-cells subsets (CD's 2, 4, 5, 7, and 8).

Figure 3A:
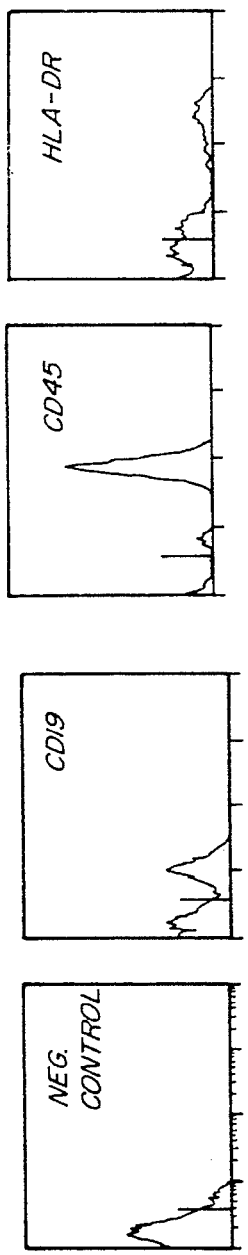
Figure 3B:
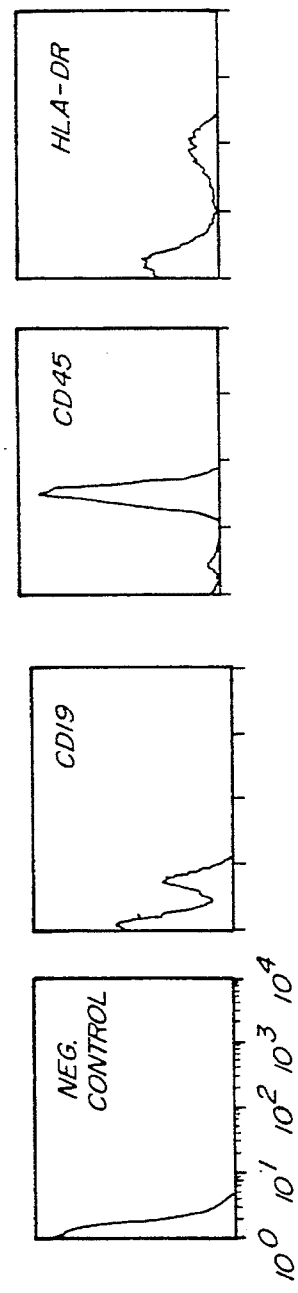

Two sets of flow cytometric evaluation were performed. The first set was performed 1 day after preservation; the results for several of these tests are shown in the top row of FIG. 3. The second set was performed 6 weeks after preservation; those results are shown in the bottom row of FIG. 3. FIG. 3 contains histograms for only some of the antigens tested; other antigens not shown in FIG. 3 provided comparable results.

These tests were performed using identical instrument settings so that a relative comparison of fluorescence intensity would be possible. The 6-week-old preparation shows a slight decrease in fluorescence intensity (FI) for all parameters tested. This decrease was detected in the negative control tests, which were performed using labelled MoAb's that did not bind to any known antigens on the cell surfaces. The decrease in FI is indicated by a shift of the peaks toward the left on each of the 6-week histograms (bottom row) compared to the peaks generated one day after cell preservation (top row) in FIG. 3.

The position of a peak along the horizontal axis can be shifted to the left or right merely by adjusting the FI gain control on a flow cytometer. If the gain (i.e., the electronic amplification of the signal detected by the optical detector) is increased, a peak on a histogram will move toward the right. Therefore, it is possible to calibrate the FI gain control (thereby adjusting the positions of the peaks) by recording the position of the FI peak position that is generated when testing a negative control sample immediately after cell preservation, and adjusting the FI gain setting to provide the same peak position when testing the negative control sample after some period of time, such as several weeks later. It can be seen from FIG. 3 that if all of the peaks in the bottom row had been shifted to the right by making an FI gain adjustment based on the negative control tests, the histograms for all antigens would have aligned very closely even after six weeks of storage.

Example 6

Preparation and Use of Normal and Abnormal Lymphoid and Non-Lymphoid Cells

A number of cell preparations were made from normal and malignant lymphoid cells. These include normal cells from tonsils, lymph nodes, and peripheral blood, as well as cell cultures of such cells. In general, the preservation procedure described in Example 1 were used, except that certain T-cell antigens were preserved by decreasing the time of chemical fixation to 1.5 hours at ambient temperature. For example, malignant cells from patients with non-T-non-B-cell Acute Lymphoblastic Leukemia (ALL) were well preserved using the shortened 1.5 hr fixation period. Histograms taken six months after preservation indicated the usual phenotype for that malignancy, displaying positive results for CD 19, CD 10, HLA-DR, and CD 45 antigens. Cells from patients having Chronic Lymphocytic Leukemia (CLL) tend to be difficult to analyze, due to antigen instability which occurs even in freshly harvested cells which have not been treated with any fixation or preservation reagents. They are correspondingly difficult to preserve using the method of this invention, since the antigen expression following fixation is diminished further; however, despite that problem, they can be preserved by the methods described herein and analyzed with some degree of success.

Cells from patients with lymphomas have been preserved with reliable results using the protocol described in Example 1.

Cells from a number of non-lymphoid malignancies have also been successfully preserved by the methods described ehrein, including cells from patients having Chronic Myelogenous Leukemia (CML) and various forms of Acute Myeloblastic Leukemia (AML) and Acute Myelomonocytic Leukemia (AMML). In the case of CML, the cells preserved are a mixture of immature and mature granulocytic cells as well as lymphocytes. Cells taken from patients having AML (or from patients having Acute Megakaryoblastic Leukemia) include immature myeloblasts as well as M7 cells.

In all cases of non-lymphoid malignancies, the fixation protocol described in Example 1 was modified by performing all steps at 4° C. for the times specified in Example 1, and by doubling the concentrations of proteinase inhibitors in the PI solutions. This was done because such cells usually contain larger quantities of hydrolytic enzymes capable of degrading surface antigens. Histograms taken shortly after preservation and again 12 months after preservation indicated that the preservation methods performed well.

Example 7

Use of Microwave Radiation Instead of Formalin

Cell cultures of the human B-cell line RPMI 1788 (American Type Culture Collection, Bethesda, Md.) were grown in suspension culture and treated in a manner identical to the treatment described in Example 1, with the following exception. After the initial treatments with the PI solution, instead of adding a cell suspension to an excess of buffered formalin in the PI solution, the cells were treated with microwave radiation instead. No formalin was used at any time during the preservation of these cells.

The cells were irradiated in the following manner. Cells were suspended at a concentration of $10^7$ cells/mL in RPMI 1640 tissue culture medium (which contains a small quantity of protein from fetal calf serum). The three PI reagents (sodium azide, PMSF, and EDTA) and the DTT stabilizer were added to the suspension to obtain the same final concentrations specified in Example 1. The cell suspension was divided into aliquots containing 1 to 5 mL each. These were placed in plastic tubes normally used for centrifuging. A single tube with no cap or stopper was placed in a 250 ml beaker containing about 100 mL of distilled water at room temperature. The beaker was placed on a rotary table inside a microwave, to ensure that the radiation was distributed fairly evenly throughout the cell suspensions. The beaker was placed inside a 700 watt microwave oven with a shut-off switch that could be actuated by a temperature probe (Kenmore brand from Sears). The beaker and cell suspension were irradiated at high power, usually for an average of about 45 seconds, until the temperature of the water surrounding the cells reached 70° C., at which time the temperature probe shut off the oven. The beaker was promptly removed from the oven, and the plastic tube holding the cells was removed from the hot water, cooled by immersing it partially into a beaker of cold tap water, then placed inside a refrigerator maintained at 4° C. No quenching agent was added after the microwave radiation; the FCS protein in the culture medium presumably served as quenching agents.

Cell samples were tested shortly thereafter, and again several weeks later, using the immunostaining and flow cytometric analyses described above in Example 2. The histograms generated by both sets of tests indicated that the irradiation treatment in combination with the protease inhibitors effectively preserved the cells without substantial alteration of the antigens on the cell surfaces.

Example 8

Use of Detergents to Enable Nucleic Acid Analysis

The method of cell fixation described in Example 1, which preserves surface antigens, may be modified by the addition of certain types of detergents or other surfactants which can render cell membranes permeable without destroying the cells. This allows certain types of nucleic acid staining compounds such as propidium iodide (PI) to enter the cell and interact with DNA.

Figure 4A:
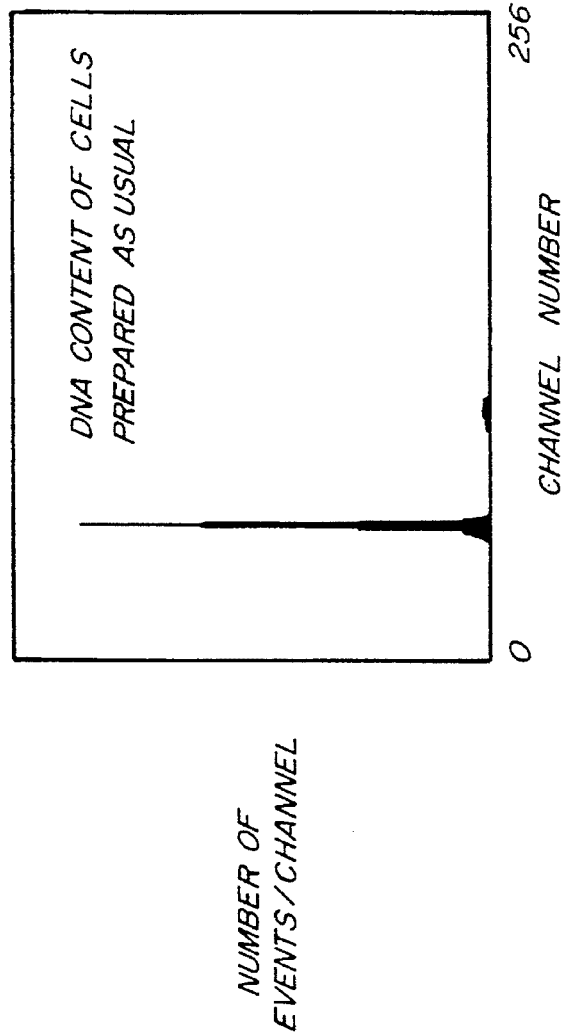

FIG. 4 shows two fluorescence histograms obtained using RPMI 1788 cells. The histogram on the left (FIG. 4a) was obtained by fixing the cells using a standard technique which involved incubating the cells in cold ethanol for 30 minutes to generate cell membrane permeability, then staining the cells with propidium iodide.

The right histogram was obtained using cells which were preserved as described in Example 1. A membrane-modifying non-ionic detergent (NP-40, sold by Sigma Chemical Company, St. Louis) was added to the suspension (0,005% v/v). After about 30 minutes, the detergent was removed by centrifuging the cells into a pellet and discarding the supernatant, and the cells were resuspended in the PI solution described in Example 1. They were either stained with propidium iodide and analyzed in a flow cytometer within a day, or they were refrigerated for subsequent staining and analysis after a prolonged storage period.

The histogram on the right (FIG. 4b) was obtained using cells that were stained within a day after the completion of the preservation and staining procedure. As shown, there is no significant difference in the histograms obtained before and after the preservation treatment. Similar histograms were obtained from cells that were stored at 4° C. for more than a year after the cells were preserved and rendered permeable. Those histograms confirmed that even after the cell membranes are rendered permeable, the cells can be stored for long periods and then used as preserved cell reagents for nucleic acid analysis.

Thus, there has been shown and described a method for preserving cells in a non-frozen, hydrated, metabolically inactive form with low levels of alteration of their antigens or nucleic acids. The present invention therefore fulfills all the objects and advantages set forth above. It will be apparent to those skilled in the art that various changes and modifications to the specific reagents and techniques described herein are possible. Any such changes that do not depart from the spirit and scope of the invention are deemed to be covered by the invention, which is limited only by the claims that follow.

REFERENCES

Caldwell, C. W., et al, "Fluorescence intensity as a quality control parameter in clinical flow cytometry," *Amer. J. Clin. Pathology* 88:447 (1988)

Feldman, A. D. and Dapson, R. A., "The Chemistry and Fixation of Staining," Parts I and II, *Journal of Histotechnology* 3:132 (1980)

Harvath, "Quality control in clinical flow cytometry," *Pathology and Immunopathology Research* 7:338 (1988)

Leong, A. S.-Y., "Microwave Irradiation in Histopathology," *Path. Ann.* 23:213 (1988)

Melamed et al, eds., *Flow Cytometry and Sorting*, 2nd edition, Wiley and Liss, New York (1990)

Schroff et al, "Detection of intra-cytoplasmic antigens by flow cytometry," *J. Immunological Methods* 70:167 (1984)

I claim:

1. A method of preserving cells to render them useful for subsequent immunologic analysis, wherein the cells express cellular proteins which function as antigenic determinants that can be used to characterize the cells by binding to complementary monoclonal antibodies, comprising the following treatment steps:
   a. treating a population of cells with at least one protease inhibitor under conditions which allow said protease inhibitor to chemically react with cellular enzymes to an extent which inhibits cell-related proteolytic activity;
   b. contacting the cells which have been treated with a chemical crosslinking agent while the cells are being agitated under conditions which promote the formation of molecular bonds within a single cell while inhibiting the formation of crosslinking bonds between different cells; and,
   c. contacting the cells with a quenching compound that will inhibit subsequent crosslinking,
      wherein said treatment steps do not substantially alter the ability of the cellular proteins to bind to complementary monoclonal antibodies.

2. The method of claim 1 wherein at least two different protease inhibitors are user to treat the cells.

3. The method of claim 1 wherein at least one protease inhibitor is selected from the group consisting of sodium azide, phenylmethylsulfonyl fluoride, and ethylenediaminetetraacetate.

4. The method of claim 1 wherein the first protease inhibition treatment is carried out in an aqueous solution that also contains a stabilizing agent comprising a compound which contains sulfhydryl groups.

5. The method of claim 4 wherein the stabilizing agent is selected from the group consisting of dithiothreitol, cysteine, and 2-mercaptoethanol.

6. The method of claim 1 wherein the crosslinking agent comprises an aldehyde compound.

7. The method of claim 6 wherein the crosslinking agent comprises formaldehyde.

8. The method of claim 1 wherein the cells are stored, after the crosslinking agent is removed, in a solution containing at least one protease inhibitor which remains in contact with the cells throughout a storage period until the cells are needed for analysis.

9. The method of claim 1 wherein the cells are contacted, after the crosslinking agent is removed, with a membrane-modifying agent that renders membranes of the cells permeable.

10. The method of claim 9 wherein the membrane-modifying agent comprises a detergent.

11. A population of cells which has been treated by the method of claim 1.

12. A population of cells which has been treated by the method of claim 4.

13. A population of cells which has been treated by the method of claim 8.

\* \* \* \* \*

UNITED STATES PATENT AND TRADEMARK OFFICE
CERTIFICATE OF CORRECTION

PATENT NO. : 5,478,722
DATED : December 26, 1995
INVENTOR(S) : Charles W. Caldwell It is certified that error appears in the above-indentified patent and that said Letters Patent is hereby corrected as shown below:

Column 14, line 28, "cube" should be -- tube --.

Column 21, line 11, "0,005%" should be -- 0.005% --.

Column 22, line 24, "user" should be -- used --.

Signed and Sealed this

Ninth Day of April, 1996

BRUCE LEHMAN

Attest:

Attesting Officer

Commissioner of Patents and Trademarks